US00PP10927P

United States Patent [19]

Pouw

[11] Patent Number: Plant 10,927

[45] Date of Patent: Jun. 1, 1999

[54] HYBRID TEA ROSE PLANT NAMED 'PANNARAN'

[75] Inventor: A. A. Pouw, De Kwakel, Netherlands

[73] Assignee: Panorama Roses N.V., Curaco, Netherlands

[21] Appl. No.: 08/982,577

[22] Filed: Dec. 2, 1997

[51] Int. Cl.[6] ..... A01H 5/00

[52] U.S. Cl. ..... Plt./130

[58] Field of Search ..... Plt./11, 12, 16, Plt./17, 18, 130, 131, 137, 136, 135, 138

[56] References Cited

U.S. PATENT DOCUMENTS

P.P. 9,326 10/1995 Zary ..... Plt./11

*Primary Examiner*—Howard J. Locker

*Attorney, Agent, or Firm*—Christie, Parker & Hale, LLP

[57] ABSTRACT

A new variety of Hybrid Tea rose plant producing pink blend flowers of good form and suitable for growing under glass.

1 Drawing Sheet

BACKGROUND OF THE INVENTION

The present invention relates to a new and distinct variety of rose plant of the Hybrid Tea rose class which was created by crossing undistributed, unnamed and upatented seedlings as seed and pollen parents in Quito, Ecuador. The varietal denomination of the new variety is 'Pannaran'. The new variety was isolated and asexually reproduced by budding in Quito, Ecuador.

SUMMARY OF THE INVENTION

Among the novel characteristics possessed by this new variety which distinguish it from its parents and all other varieties of which I am aware are its attractive pink blend flowers of good form with long stems borne on a floriferous plant and suitable for production of cut flowers under glass.

Asexual reproduction by budding of the new variety as performed in Quito, Ecuador, shows that the foregoing and other distinguishing characteristics come true to form and are established and transmitted through succeeding propagations. The new variety has been reproduced through propagation by cuttings, grafting, budding and micropropagation.

BRIEF DESCRIPTION OF ILLUSTRATION

The accompanying illustration shows a typical specimen of the vegetative growth and flower of the new variety as a cut flower, depicted in color as nearly true as it is reasonably possible to make the same in a color illustration of this character.

DESCRIPTION OF THE NEW VARIETY

The following is a detailed description of the new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart. Phenotypic expression may vary depending upon growing conditions under different climate, soil, and cultivation conditions.

Parentage: Seed and pollen parents are unnamed seedlings.
Class: Hybrid Tea.

The following further horticultural description is based on observations made of specimens grown under glass in Quito, Ecuador.

Flower

Blooming habit: Nearly continuous; about 210 stems/m$^2$/year.

A. Bud:

(1) *Size.*—Medium, about 4 to 5 cm long by about 2 to 3 cm wide, before sepals separate.

(2) *Form.*—Ovate (shape of longitudinal section just before separation of sepals); urn-shaped after sepals part and petals begin to separate.

(3) *Color.*—After sepals separate, near 18C to 18B with near 35A to 35B at edge, becoming deeper yellow toward point of petal attachment.

(4) *Sepals.*—Longer than bud, some very much longer, some foliaceous; near 147A on top surface.

(5) *Peduncle.*—Long, about 9 cm; Strength-erect, strong. Color-medium green, near 138A.

B. Flower: Medium; viewed from above — star-rounded; viewed from side — (a) upper part of fully opened flower, flattened convex; (b) lower part of fully opened flower, concave.

(1) *Size.*—Average size when fully expanded — about 12 to 13 cm at about full open.

(2) *Borne.*—Singly, one to a stem, stem length about 50 to 71 cm.

(3) *Form.*—Pointed center, spiral imbricated, some outer petals reflex to points, some petals roll under center pointed until fully open.

(4) *Petalage.*—Fully double, about 25 petals.

(5) *Color.*—After sepals part and petals unfurl: young flower, upper margin near 25A and upper middle near 25A, lower margin near 25B to 25C and lower middle near 26C; open flower, upper margin near 52C to 52D and upper middle near 49A, lower margin near 49B and lower middle near 49C. Petal undersurface continues to exhibit yellow coloration. Color at point of petal attachment is near 12A to 10A. Overall tonality from a distance is attractive pink blend with apricot tones.

(6) *Peduncle.*—Very slight roughness.

(7) *Fragrance.*—Absent or weak.

(8) *Length of stems.*—About 60 to 100 cm.

Petals:

(1) *Texture.*—Crisp.

(2) *Appearance.*—Inside velvety and outside satiny.

(3) *Form and size.*—Broad, medium, weak undulation of margin.

(4) *Arrangement.*—Regularly arranged, imbricated.

(5) *Petaloids.*—About seven, same color as petals.

(6) *Lasting quality.*—About 14 days on plant and about 10 days after cutting.

Reproductive Organs

A. Stamens, filaments and anthers:

*Arrangement and color.*—Regularly arranged around styles; color of filaments — orange red.

B. Pollen:

*Color.*—Yellow.

C. Styles: Long, stigma above mouth of receptacle, pale yellow.

D. Stigmas: Yellow, positioned below anthers.

E. Hip: Pitcher-shaped; small seed vessel at petal fall.

Plant

A. Form: Narrow, bushy, average disease resistance; height about 121 cm, spread about 40 cm.

B. Growth: Vigorous.

C. Foliage: Compound 3, 5 and 7 leaflets.

(1) *Size.*—3-leaflet leaf, terminal leaflet about 7 to 8 cm long; 5-leaflet leaf, terminal leaflet about 9 to 10 cm long; 7 leaflet leaf, terminal leaflet about 6 to 7 cm long.

(2) *Quantity.*—Abundant.

(3) *Color.*—Juvenile foliage — upper side near 187A, underside near 59A; weak anthocyanin coloration, (shoot about 3 inches long); mature leaf color — upper side near 139A, underside near 147B.

(4) *Shape.*—Broad oval.

(5) *Texture.*—Upper side is weak to medium glossy; underside is matte.

(6) *Edge.*—Serrate.

(7) *Serration.*—Ordinary, acuminate apices.

(8) *Leaf stem.*—Color — near 139B.

(9) *Stipules.*—Short, simple, medium green.

(10) *Leaflets.*—Cross section — flat, medium undulation of margin; terminal leaflet — medium length and medium width; round base.

D. Wood:

(1) *New wood.*—Color — young shoots have weak anthocyanin; coloration — bronze red purple to reddish brown.

(2) *Old wood.*—Color — near 139B to 139C.

E. Prickles (thorns):

(1) *Prickles.*—Present; quantity (main stalk) — ordinary; shape of lower side — concave; Quantity — short prickles absent or very few, long prickles medium; Color — near 193A; Position — irregular.

What is claimed is:

1. A new and distinct rose plant of the variety substantially as shown and described.

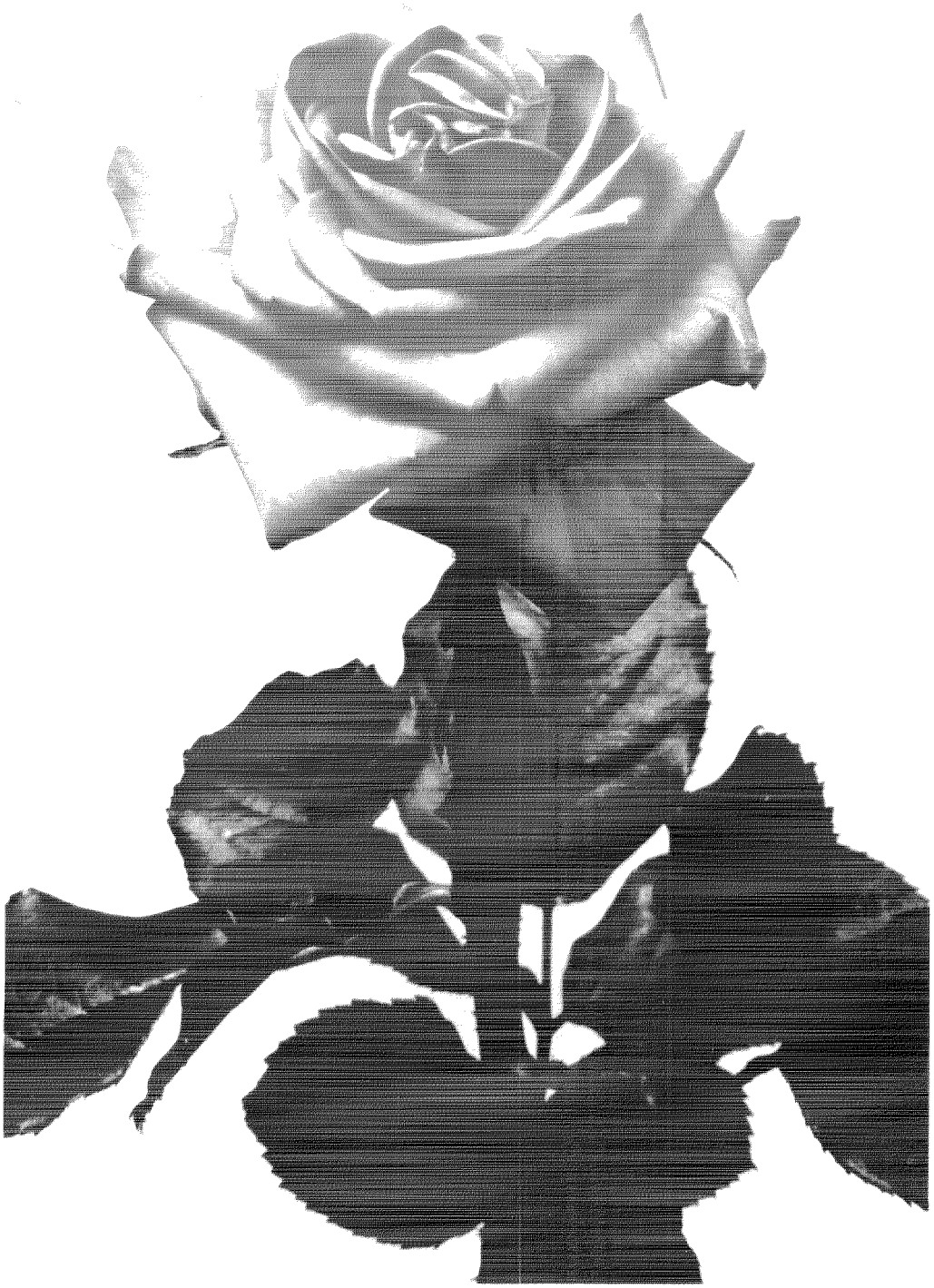

* * * * *